United States Patent [19]
Denzel et al.

[11] B 3,984,412
[45] Oct. 5, 1976

[54] AMINO DERIVATIVES OF PYRIDO[2,3-B]PYRAZINE CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[22] Filed: July 25, 1974

[21] Appl. No.: 491,883

[44] Published under the second Trial Voluntary Protest Program on February 3, 1976 as document No. B 491,883.

[52] U.S. Cl. ..................... 260/250 BC; 260/295 R; 424/200; 424/232; 424/250
[51] Int. Cl.$^2$........................................ C07D 487/04
[58] Field of Search .............................. 260/250 BC

[56] References Cited
UNITED STATES PATENTS
3,180,868  4/1965  Osdeng et al. ................ 260/250 BC Primary Examiner—R. J. Gallagher
Attorney, Agent, or Firm—Lawrence S. Levinson; Merle J. Smith

[57] ABSTRACT

New derivatives of pyrido[2,3-b]pyrazine carboxylic acids and esters and their acid addition salts have the general formula

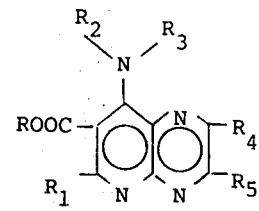

They are useful as anti-inflammatory agents and central nervous system depressants.

10 Claims, No Drawings

AMINO DERIVATIVES OF PYRIDO[2,3-b]PYRAZINE CARBOXYLIC ACIDS AND ESTERS

SUMMARY OF THE INVENTION

The invention relates to the new amino derivatives of pyrido[2,3-b]pyrazine carboxylic acids and esters and acid addition salts thereof having the general formula (I)
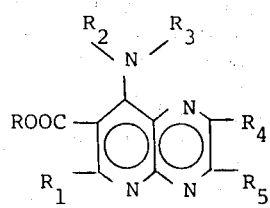

The symbols have the following meaning in formula I and throughout this specification:

The basic nitrogen group

is an acyclic amino moiety wherein $R_2$ and $R_3$ each is hydrogen, lower alkyl, lower alkanoyl, phenyl, substituted phenyl or di(lower alkylamino) lower alkyl.

R, $R_1$, $R_4$ and $R_5$ each is hydrogen or lower alkyl.

The lower alkyl groups in any of the foregoing radicals include straight or branched chain hydrocarbon groups containing 1 to 7 carbon atoms. Examples of the groups contemplated are methyl, ethyl, propyl, isopropyl etc. Lower alkyl groups of 1 to 4 carbon atoms are preferred, especially the 1 and 2 carbon members of this group. The lower alkanoyl groups are of similar type being the acyl radicals of the lower fatty acids of up to 7 carbons, $C_2$ to $C_4$ being preferred, especially acetyl. The substituted phenyl groups include one or two simple substituents (preferably only one substituent, but they are the same groups if disubstituted), i.e., lower alkyl, lower alkoxy, halogen (F, Cl, Br or I, preferably Cl or Br), $CF_3$, amino or carboxy. Examples of the types of groups contemplated are o-, m- or p-chlorophenyl, o-, m- or p-tolyl, 2,5-dichlorophenyl, 3,5-dimehtylphenyl or 3,4-dimethoxyphenyl.

Preferred embodiments of this invention are as follows:

R is hydrogen or lower alkyl of 1 to 4 carbon atoms, especially ethyl.

$R_1$ is lower alkyl, especially methyl.

$R_2$ and $R_3$ each is hydrogen, lower alkyl of 1 to 4 carbon atoms, especially butyl or di(lower alkyl)amino(lower alkyl), especially dimethylaminopropyl.

$R_4$ and $R_5$ each is hydrogen or lower alkyl, especially hydrogen and methyl.

DETAILED DESCRIPTION

The new compounds of formuls I are formed by the following series of reactions. The symbols in the structural formulas have the same meaning as previously described.

A 4,6-dihydroxypyridine carboxylic acid ester of the formula (II)
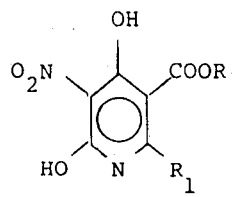

[produced analogous to the procedure described in Chem. Ber. 99, 244 (1966)]wherein R is lower alkyl, is made to react with an inorganic acid chloride like phosphorus oxychloride, producing a compound of the formula:

(III)
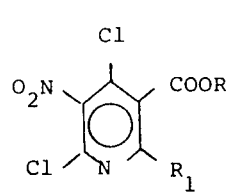

with two chlorine atoms in the 4- and 6-positions of the molecule. This compound is now treated with an amine of the formula (IV)

in the presence of a base, e.g., an alkylamine like triethylamine, forming a compound of the formula (V)
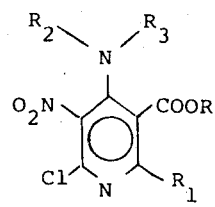

Reaction of the compound of formula V with gaseous or aqueous ammonia in an alcohol solvent like butyl alcohol produces a compound of the formula (VI)
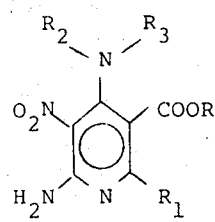

Sometimes it is necessary to use an autoclave.

Hydrogenation of this product either catalytically or with a metal-acid pair like zinc in acetic acid results in the formation of a compound of the formula:

(VII)

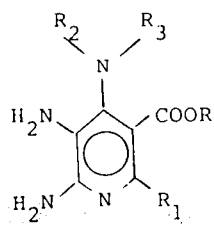

The compound of formula I is now produced by reacting the compound of formula VII with an appropriate 1,2-diketone of the formula (VIII)

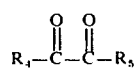

The water formed by this reaction is removed by a water-separator using an aromatic solvent like benzene or toluene.

Compounds of formula VII wherein $R_2$ and $R_3$ are both hydrogen can be produced by an alternate process. In this case the compound of formula III is treated with t-butyl amine. A product of formula V is obtained wherein $R_2$ is t-butylamine and $R_3$ is hydrogen. This product is then processed as described above, i.e., reaction with ammonia, hydrogenation and treatment with the 1,2-diketone of formula VIII. This series of reactions produces a compound of formula I with a t-butylamino group in the 4-position. A compound of formula I wherein $R_2$ and $R_3$ are both hydrogen is now produced by heating the t-butylamino compound for about five minutes at a temperature of about 250°–260°C.

The ester can be converted to the acid, i.e., wherein R is hydrogen, with a dilute alkali hydroxide like sodium hydroxide.

The bases of formula I form physiologically acceptable acid addition salts by reaction with an equivalent amount of one of the common inorganic and organic acids. Such salts include the hydrohalides, e.g., hydrobromide, hydrochloride, sulfate, nitrate, phosphate, acetate, citrate, oxalate, tartrate, maleate, succinate, benzoate, ascorbate, alkanesulfonate, e.g., methanesulfonate, arylsulfonate, e.g., benzenesulfonate, etc. It is frequently convenient to purify or isolate the product by forming an insoluble salt which is not necessarily physiologically acceptable. The base is then obtained by neutralization and another salt can then be formed by treatment with the appropriate inorganic or organic acid.

The new compounds of this invention have antiinflammatory properties and are useful, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They are compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream can also be used.

The compounds of this invention are also central nervous system depressants and can be used as tranquilizers or ataractic agents for the relief of anxiety and tension states, for example, in mice, cats, rats, dogs and other mammalian species. For this purpose, a compound or mixture of compounds of formula I, or nontoxic, physiologically acceptable acid addition salt thereof, is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. A conventional dosage in oral or parenteral form is compounded by incorporating about 10 to 250 mg. per unit of dosage with conventional vehicle, excipient, binder, preservative, stabilizer, flavor or the like as called for by accepted pharmaceutical practice.

The following examples constitute preferred embodiments and also illustrate how these and other members of the group are produced. Simple variation of the reactants and substitution in the reaction sequences described below readily yield other compounds within the scope of the invention. All temperatures are in degrees celsius.

EXAMPLE 1

8-Butylamino[2,3,6]-trimethylpyrido[2,3-b]pyrazine-7-carboxylic acid, ethyl ester a)

4,6-Dichloro-2-methyl-5-nitropyridine-3-carboxylic acid ethyl ester 242 g. of 4,6-Dihydroxy-2-methyl-5-nitropyridine-3carboxylic acid ethyl ester (1 Mol.) are heated at 120° with 500 ml. of phosphorus oxychloride for 3 hours. After this time, the excess phosphorus oxychloride is removed in vacuo and the black residue is decomposed by pouring into ice water. About 1 liter of chloroform is added and the mixture is filtered to remove undissolved material. The organic layer is separated and the aqueous phase is extracted twice with 100 ml. portions of chloroform. The extract is dried over calcium chloride, filtered and evaporated to dryness. The resulting oil is cyrstallized with about 500 ml. of petroleum ether yielding 153 g. of 4,6-dichloro-2-methyl-5-nitropyridine-3-carboxylic acid ethyl ester (55%); m.p. 45°–46°.

b)

4-Butylamino-6-chloro-2-methyl-5-nitropyridine-3-carboxylic acid, ethyl ester 139.5 g. of 4,6-Dichloro-2-methyl-5-nitropyridine-3-carboxylic acid ethyl ester (0.5 m.) are dissolved in about 500 ml. of methanol. 60 g. of triethylamine are added and the solution is heated at reflux temperature. At this point 36.5 g. of n-butylamine are dropwise. The solvent is then removed in vacuo and 500 ml. of benzene are added to the residue. The triethylamine hydrochloride is filtered off and the solvent evaporated. The resulting oil is dissolved in 300 ml. of methanol and yields on cooling 100 g. of 4-butylamino-6-chloro-2-methyl-5-nitropyridine-3-carboxylic acid, ethyl ester (70%); m.p. 33°–35° (methanol).

c)
6-Amino-4-butylamino-2-methyl-5-nitropyridine-3-carboxylic acid, ethyl ester 177.9 g. of 4-butylamino-6-chloro-2-methyl-5-nitropyridine-3-carboxylic acid, ethyl ester (0.5 Mol.) dissolved in 500 ml. of methanol are heated with 300 ml. of aqueous ammonia (30%) in an autoclave at about 60° for 10 hours. After this time, the solvent is distilled off and the residual 6-amino-4-butylamino-2-methyl-5-nitropyridine-3-carboxylic acid, ethyl ester is recrystallized from methanol, yield 135 g.; m.p. 98°–99°.

d)
5,6-Diamino-4-butylamino-2-methylpyridine-3-carboxylic acid, ethyl ester 29.6 g. of 6-Amino-4-butylamino-2-methylpyridine-3-carboxylic acid, ethyl acid, (0.1 Mol.) are dissolved in 150 ml. of acetic acid. The solution is heated at reflux temperature. Zinc is added carefully until the mixture is colorless (about 20 g.). Heating is continued for an additional 10 minutes. The mixture is then evaporated to dryness and about 100 ml. of water are added. The solution is neutralized with dilute aqueous ammonia and extracted three times with 100 ml. portions of ether. The ether extracts are combined, dried with calcium chloride and the solvent evaporated. The oily residue, 5,6-diamino-4-butylamino-2-methylpyridine-3-carboxylic acid, ethyl ester crystallized from methanol, yield 21 g. (79%); m.p. 82°–83°.

e)
8-Butylamino-2,3,6-trimethylpyrido[2,3-b]pyrazine-7-carboxylic acid, ethyl ester 26.6 g. of 5,6-Diamino-4-butylamino-2-methylpyridine-3-carboxylic acid, ethyl ester (0.1 Mol) are dissolved in 150 ml. of toluene. 9 g. of diacetyl are added and the mixture is refluxed while the water formed is removed by a water separator. After about 5 hours, the theoretical amount of water is separated and the solution is evaporated to dryness. The dark oily residue is extracted twice with 100 ml. portions of gasoline and addition of activated charcoal. The gasoline extracts are combined and concentrated to about 100 ml. 8-Butylamino-2,3,6-trimethylprido[2,3-b]pyrazine-7-carboxylic acid, ethyl ester crystallizes on cooling, yield 21 g. (66%); m.p. 97°–99°.

EXAMPLE 2

8-Butylamino-6-methylpyrido[2,3-b]pyrazine-7-carboxylic acid, ethyl ester 13.3 g. of 5,6-Diamino-4-butylamino-2-methylpyridine-3-carboxylic acid, ethyl ester (0.05 Mol.) of Example 1 d and 4g. of glyoxal monohydrate, dissolved in 100 ml. of toluene, are refluxed, while the water formed is removed by means of a water separator. After about 3 hours, the reaction is complete and the solution is concentrated. The remaining oily residue is extracted twice with 50 ml. portions of gasoline and addition of activated charcoal. The gasoline extracts are cooled and the crystalline 8-butylamino-6-methylpyrido[2,3-b]pyrazine-7-carboxylic acid, ethyl ester is filtered off, yield 70%; m.p. 56°–58°.

EXAMPLE 3

8-Ethylamino-6-methylpyrido[2,3-b]pyrazine-7-carboxylic acid ethyl ester

By substituting ethylamine for the butylamine in the procedure of Example 1 b, 6-chloro-4-ethylamino-2-methyl-5-nitropyridine-3-carboxylic acid, ethyl ester is obtained; m.p. 35°–36°. This product is processed as described in Example 1 c – e. This results in the formation of 8-ethylamino-6-methylpyrido[2,3-b]pyrazine-7-carboxylic acid, ethyl ester; m.p. 72°–74° (gasoline).

EXAMPLE 4

8-[[3-(Dimethylamino)propyl]amino]-6-methyl-pyrido[2,3-b]-pyrazine-7-carboxylic acid, ethyl ester a)
6-Chloro-4-[[3-(dimethylamino)propyl]amino]-2-methyl-5-nitropyridine-3-carboxylic acid, ethyl ester 139.5 g. of 4,6-dichloro-2-methyl-5-nitropyridine-3-carboxylic acid, ethyl ester (0.5 ml.) in 500 ml. of ethyl alcohol are heated at reflux temperature. 60 g. of triethylamine are added and then 51 g. of 3-(dimethylamino)propylamine are slowly dropped in with stirring. After the addition is completed, heating is continued for 10 minutes. The solvent is distilled off and the residue is treated with 200 ml. of water and made alkaline (pH 9-10) with sodium hydroxide. This mixture is extracted three times with 150 ml. portions of ether. The organic layers are combined, dried with calcium chloride and evaporated to dryness. The residue is recrystallized from methanol, yield 110 g. (64%); m.p. <20°.

b)
6-Amino-4-[[3-diemethylamino)propyl]amino]2-methyl-5-nitropyridine-3-carboxylic acid, ethyl ester 6-Chloro-4-[[3-(dimethylamino)propyl]amino]-2-methyl-5-nitropyridine-3-carboxylic acid, ethyl ester is treated with ammonia according to the procedure of Example 1 c and 6-amino-4-[[3-(dimethylamino)-propyl]amino]-2-methyl-5-nitropyridine-3-carboxylic acid, ethyl ester, hydrochloride is obtained, m.p. 182° (dec.), (methanol). The aqueous solution of this hydrochloride is made alkaline with sodium hydroxide and extracted with ether to obtain the free base, m.p. 52°–53° (methanol).

c)
5,6-Diamino-4-[[3-(dimethylamino)propyl]amino]-2-methylpyridine-3-carboxylic acid, ethyl ester 31.1 g. of 6-Amino-4[3-(dimethylamino)propyl-]amino-2-methyl-5-nitropyridine-3-carboxylic acid, ethyl ester are dissolved in 200 ml. of butyl alcohol. 0.5 g. of palladium on charcoal (10%) are added and the mixture is hydrogenated at 90° and a hydrogen pressure of 3 at. When the theoretical amount of hydrogen has been absorbed, the catalyst is filtered off and the mixture evaporated to dryness. The resulting 5,6-diamino-4-[[3-(dimethylamino)propyl]amino]-2-methylpyridine-3-carboxylic acid, ethyl ester is used without further purification.

d)

8-[[3-(Dimethylamino)propyl]amino]-6-methyl-pyrido[2,3-b]-pyrazine-7-carboxylic acid, ethyl ester 3 g. of crude 5,6-diamino-4-[[3-(dimethylamino)-propyl]-amino]-2-methylpyridine-3-carboxylic acid, ethyl ester and 1 g. of glyoxal-monohydrate are refluxed in 20 ml. of toluene for 4 hours. After evaporation of the solvent and addition of a small amount of charcoal, the residue is extracted with 50 ml. of boiling gasoline. On cooling 8-[[3-(dimethylamino)propyl-]amino]-6-methylpyrido[2,3-b]pyrazine-7-carboxylic acid, ethyl ester precipitates, m.p. 42°–44° (gasoline).

The following additional products are obtained by the procedure of Example 1:

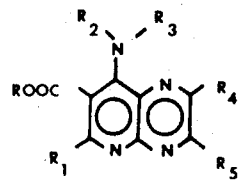

| Example | R | $R_1$ | $N{<}^{R_2}_{R_3}$ | $R_4$ | $R_5$ |
|---|---|---|---|---|---|
| 5 | H | $C_2H_5$ | —NH—$C_4H_9$ | H | H |
| 6 | $C_2H_5$ | $CH_3$ | —$NH_2$ | $CH_3$ | H |
| 7 | $C_2H_5$ | H | —NH—$C_2H_5$ | $CH_3$ | $CH_3$ |
| 8 | $C_2H_5$ | $CH_3$ | —NH—$C_3H_7$ | H | $CH_3$ |
| 9 | H | H | —NH—$C_4H_9$ | H | H |
| 10 | $C_2H_5$ | $CH_3$ | —$N(CH_3)_2$ | H | H |
| 11 | $C_2H_5$ | $C_2H_5$ | —$N(C_2H_5)_2$ | H | H |
| 12 | $C_2H_5$ | $CH_3$ | $NHCOCH_3$ | H | H |
| 13 | H | $CH_3$ | $N(COCH_3)_2$ | H | $CH_3$ |
| 14 | H | i—$C_3H_7$ | —NH—C$_6$H$_5$ | H | H |
| 15 | $C_2H_5$ | H | —NH—C$_6$H$_4$—$CF_3$ | $CH_3$ | $CH_3$ |
| 16 | H | $C_2H_5$ | —NH—C$_6$H$_4$—COOH | H | H |
| 17 | $CH_3$ | $C_2H_5$ | —NH—C$_6$H$_4$—$CH_3$ | H | H |
| 18 | $C_2H_5$ | $CH_3$ | $N(C_6H_5)_2$ | H | H |
| 19 | $C_2H_5$ | $CH_3$ | NH—C$_6$H$_3$(CH$_3$)$_2$ | H | H |
| 20 | $C_2H_5$ | $CH_3$ | NH—C$_6$H$_3$(OCH$_3$)$_2$ | H | H |
| 21 | $C_2H_5$ | H | NH—C$_6$H$_4$—Cl | H | H |

-continued-

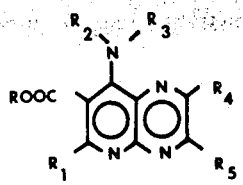

| Example | R | $R_1$ | $N\begin{smallmatrix}R_2\\R_3\end{smallmatrix}$ | $R_4$ | $R_5$ |
|---|---|---|---|---|---|
| 22 | $CH_3$ | $CH_3$ |  NH—C₆H₃(Br)₂ | H | H |
| 23 | H | $CH_3$ | 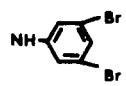 —NH—C₆H₄—NH₂ | H | H |
| 24 | $C_3H_7$ | $C_2H_5$ | —NH—CH₂CH₂N(C₂H₅)₂ | $C_2H_5$ | H |
| 25 | $C_2H_5$ | H | NHCH₂CH₂N(CH₃)₂ | $CH_3$ | $CH_3$ |
| 26 | H | $CH_3$ | NHCH₃ | H | H |
| 27 | H | $CH_3$ |  NH—C₆H₄—CH₃ | H | H |
| 28 | $C_2H_5$ | $C_2H_5$ |  NH—C₆H₅ | H | H |
| 29 | H | $C_2H_5$ | NH(CH₂)₃N(C₂H₅)₂ | H | H |
| 30 | $C_2H_5$ | CH₂CH₂CH(CH₃)₂ | NHC₄H₉ | H | H |

What is claimed is:

1. A compound of the formula

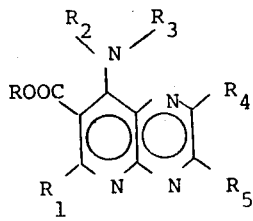

wherein R, $R_1$, $R_4$ and $R_5$ each is hydrogen or lower alkyl; $R_2$ and $R_3$ each is hydrogen, lower alkyl, lower alkanoyl, di(lower alkylamino)lower alkyl, phenyl or substituted phenyl; wherein the substituted phenyl bears one or two lower alkyl, lower alkoxy, halogen, trifluoromethyl, amino or carboxy groups; and phsiologically acceptable acid addition salts thereof.

2. A compound as in claim 1 wherein R is hydrogen or lower alkyl of 1 to 4 carbon atoms; $R_2$ and $R_3$ each is hydrogen, lower alkyl of 1 to 4 carbon atoms, or di(lower alkylamino)lower alkyl; and $R_4$ and $R_5$ each is hydrogen or lower alkyl.

3. A compound as in claim 1 wherein $R_1$, $R_2$, $R_4$ and $R_5$ is lower alkyl and $R_3$ is hydrogen.

4. A compound as in claim 1 wherein R is ethyl, $R_1$, $R_4$ and $R_5$ each is methyl, $R_2$ is butyl and $R_3$ is hydrogen.

5. A compound as in claim 1 wherein R, $R_1$, and $R_2$ each is lower alkyl and $R_3$, $R_4$ and $R_5$ each is hydrogen.

6. A compound as in claim 1 wherein R is ethyl, $R_1$ is methyl, $R_2$ is butyl and $R_3$, $R_4$ and $R_5$ each is hydrogen.

7. A compound as in claim 1 wherein R and $R_2$ each is ethyl, $R_1$ is methyl, and $R_3$, $R_4$ and $R_5$ each is hydrogen.

8. A compound as in claim 1 wherein R and $R_1$ each is lower alkyl, $R_2$ is di(lower alkylamino)lower alkyl and $R_3$, $R_4$ and $R_5$ each is hydrogen.

9. A compound as in claim 1 wherein R is ethyl, $R_1$ is methyl, $R_2$ is dimethylaminopropyl and $R_3$, $R_4$ $R_5$ each is hydrogen.

10. A compound of the formula

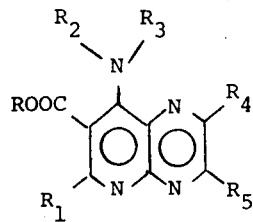

wherein R, $R_1$, $R_4$ and $R_5$ each is hydrogen or lower alkyl; $R_2$ and $R_3$ each is hydrogen, lower alkyl, lower alkanoyl, di(lower alkylamino)lower alkyl, phenyl or substituted phenyl; wherein the substituted phenyl bears one or two lower alkyl, lower alkoxy, halogen, trifluoromethyl, amino or carboxy groups.

* * * * *